US012751827B1

(12) United States Patent
Klima

(10) Patent No.: US 12,751,827 B1
(45) Date of Patent: Oct. 6, 2026

(54) REINFORCED ARTHROPLASTY STEMS WITH INTEGRATED THREADED BOSSES AND INTERNAL WALKER-TYPE COMPRESSION

(71) Applicant: Matthew Klima, Tampa, FL (US)

(72) Inventor: Matthew Lee Klima, Tampa, FL (US)

( * ) Notice: Subject to any disclaimer, the term of this patent is extended or adjusted under 35 U.S.C. 154(b) by 18 days.

(21) Appl. No.: 19/360,502

(22) Filed: Oct. 16, 2025

Related U.S. Application Data

(60) Provisional application No. 63/897,573, filed on Oct. 11, 2025, provisional application No. 63/897,742, filed on Oct. 12, 2025, provisional application No. 63/897,786, filed on Oct. 12, 2025.

(51) Int. Cl.
*A61F 2/30* (2006.01)
*A61F 2/38* (2006.01)

(52) U.S. Cl.
CPC ........ *A61F 2/30749* (2013.01); *A61F 2/3094* (2013.01); *A61F 2/3804* (2013.01); *A61F 2/3859* (2013.01); *A61F 2/389* (2013.01); *A61F 2002/30235* (2013.01); *A61F 2002/30425* (2013.01); *A61F 2002/30546* (2013.01); *A61F 2002/30604* (2013.01); *A61F 2002/30955* (2013.01); *A61F 2002/30978* (2013.01); *A61F 2002/3822* (2013.01)

(58) Field of Classification Search
CPC .. A61F 2002/30782; A61F 2002/30797; A61F 2002/30433; A61F 2002/368; A61B 18/80; A61B 17/8004; A61B 17/7225
See application file for complete search history.

(56) References Cited

U.S. PATENT DOCUMENTS 4,101,985 A * 7/1978 Baumann .................. A61F 2/34 623/22.46
5,462,547 A * 10/1995 Weigum ............... A61B 17/746 606/65
8,709,092 B2 4/2014 Segina
12,232,784 B2 * 2/2025 Yacoubian ............. A61B 17/72
2007/0123878 A1 * 5/2007 Shaver .................. A61B 17/72 606/64

(Continued)

OTHER PUBLICATIONS

CNCLaithing, Buttress Thread Chart: Metric Dimensions, Angle & Calculator, https://www.cnclathing.com/guide/buttress-thread-chart-metric-dimensions-angle-calculator (Year: 2024).*

*Primary Examiner* — Thomas C Barrett
*Assistant Examiner* — Teresa M Dudden

(57) ABSTRACT

An arthroplasty stem includes one or more integrated or sleeved threaded bosses within a metallic stem body and at least one oblique ramped (“Walker”) compression aperture. Rotation of a screw within the aperture converts rotational motion into controlled axial compression between the stem and an attached fixation plate or adapter. The threaded bosses, either machined directly into the stem or positioned within dielectric-lined sleeves, enable secure fixation without drilling through the stem wall. The invention combines threaded bosses that retain and sustain load with Walker-type ramped apertures that actively generate compression within an arthroplasty stem, creating a self-contained dynamic and static fixation system adaptable to multiple joint reconstruction applications.

12 Claims, 5 Drawing Sheets

(56) References Cited

U.S. PATENT DOCUMENTS

| | | | | |
|---|---|---|---|---|
| 2012/0265255 | A1* | 10/2012 | Hilse | A61B 17/8014 606/290 |
| 2013/0079829 | A1* | 3/2013 | Globerman | A61B 17/8033 606/286 |
| 2017/0164986 | A1* | 6/2017 | Chen | A61B 17/68 |
| 2024/0041612 | A1* | 2/2024 | Peterman | A61F 2/4425 |

* cited by examiner

REINFORCED ARTHROPLASTY STEMS WITH INTEGRATED THREADED BOSSES AND INTERNAL WALKER-TYPE COMPRESSION

FIELD OF THE INVENTION

The present invention relates to orthopedic arthroplasty systems, and more particularly to arthroplasty stems incorporating integrated and sleeved threaded bosses and internal compression apertures for secure fixation and controlled compression without compromising stem integrity.

BACKGROUND OF THE INVENTION

Conventional arthroplasty stems often rely on cement fixation or external modular collars for stabilization. When additional fixation is required-such as for periprosthetic fractures-surgeons typically drill directly into the metallic stem to insert screws or adapters. This practice weakens the stem, creating localized stress risers and initiating fatigue cracks. Titanium alloy stems are especially vulnerable to notch sensitivity, leading to premature implant failure.

Existing systems also lack an internal mechanism for generating controlled compression across bone or implant interfaces. Compression must instead be generated externally through plate constructs or tensioning devices. There remains a need for an arthroplasty stem that incorporates reinforcement bosses and internal compression apertures, allowing secure fixation and compressive control without compromising stem strength or requiring drilling.

SUMMARY OF THE INVENTION

The invention provides a reinforced arthroplasty stem system incorporating one or more threaded bosses and internal ramped ("Walker-type") compression apertures. Threaded bosses are either machined directly into the stem wall or positioned within replaceable metallic or polymer-metal sleeves. The bosses permit attachment of fixation plates, compression screws, or modular adapters without drilling into the stem body.

Each compression aperture defines an oblique or elliptical ramp such that rotation of a screw therein produces axial translation and controlled compression between the stem and an attached fixation element. The system optionally incorporates dielectric liners or coatings between dissimilar materials (e.g., titanium stem and stainless or cobalt-chrome sleeve) to prevent galvanic corrosion. Reinforcement geometries such as butterfly ribs or circumferential collars redistribute stress around boss regions an . . . .

DETAILED DESCRIPTION OF THE INVENTION

Full Functional Overview Paragraph

Figure 1:
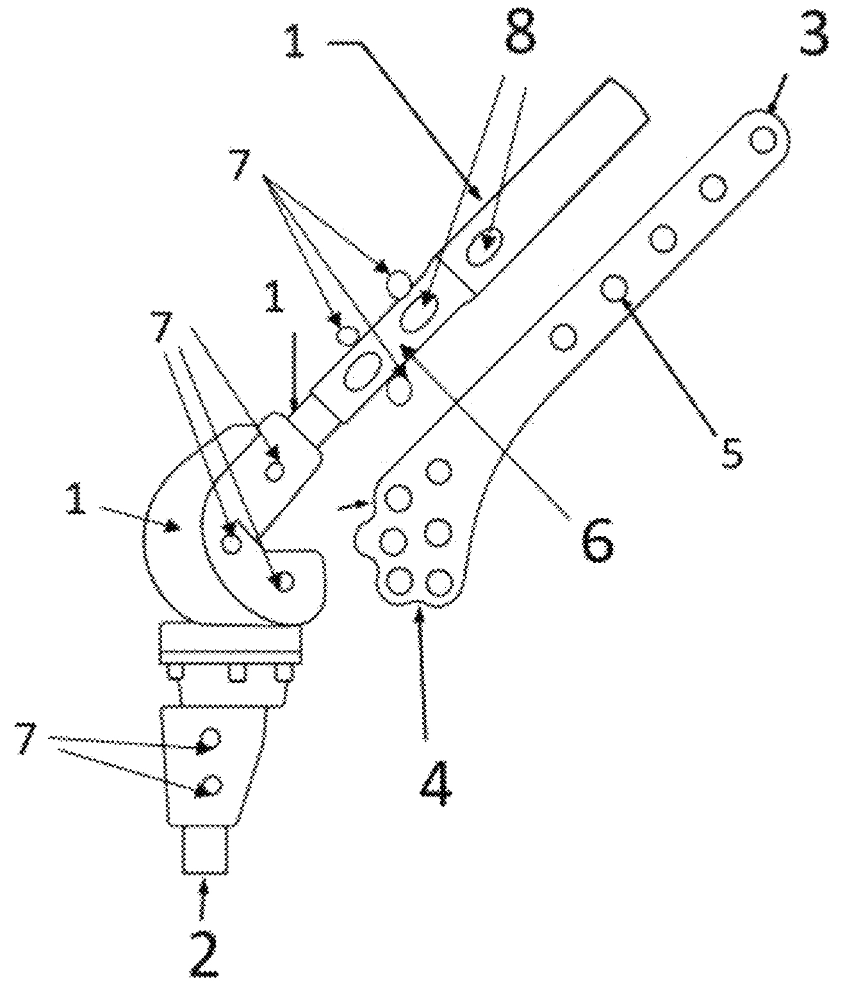
FIG. 1—Compression Boss Stem Assembly Illustrates one embodiment of a modular compression and fixation construct in which a locked plate interfaces with a reinforced stem through threaded bosses and compression apertures. The configuration allows axial compression and angular stability between the plate and stem. Although shown in a femoral-tibial configuration, the design concept is adaptable to other arthroplasty stems, including hip, knee, and shoulder systems.

The present invention integrates two distinct but cooperative mechanical systems within an arthroplasty stem: a series of threaded bosses and one or more Walker-type elliptical or ramped compression apertures. The threaded bosses function primarily as static retention and load-transfer features, securing modular plates or fixation elements to the stem and maintaining alignment during compression. In contrast, the ramped or elliptical apertures serve as the active compression-generating components, translating rotational torque from an advancing screw into controlled linear displacement that produces axial compression between modular interfaces. Once compression is achieved through the ramped aperture, the surrounding bossed region of the stem functions to retain and sustain the compressive load, thereby combining dynamic and static fixation in a unified construct. This cooperative interaction allows internal generation, maintenance, and distribution of compressive forces within the stem body, reducing reliance on external plating or tensioning instruments while preserving modularity across femoral, tibial, humeral, and other arthroplasty stems.

Stem Architecture

The arthroplasty stem may be fabricated from titanium, cobalt-chrome, or hybrid alloys. The stem includes one or more boss locations oriented medially, laterally, or anteriorly. Bosses may be machined directly into the stem body or configured to receive press-fitted or shrink-fitted sleeves. Each boss defines a threaded aperture suitable for screw engagement, plate attachment, or modular adapter coupling.

Integrated Bosses

In one embodiment, the bosses are directly machined into the solid stem body using precision EDM or thread-forming processes. The boss threads extend into reinforced material regions defined by increased wall thickness and circumferential ribbing to prevent fatigue failure. The integrated boss allows direct fixation while maintaining structural integrity through geometry-based reinforcement.

Sleeved Boss Variant

In another embodiment, the boss aperture is formed within a replaceable sleeve. The sleeve is interference-fitted or shrink-fitted into the stem and may include a dielectric liner composed of PEEK, PEKK, alumina, or other nonconductive material. The sleeve provides a replaceable interface that mitigates galvanic corrosion and distributes stress uniformly. In some embodiments, the sleeve is bonded via adhesive or thermal interference to achieve a hermetic seal.

Walker-Type Compression Aperture

Each stem may include an oblique or ramped aperture extending through the stem body. The aperture includes a ramp geometry defining an angle θ of approximately 20°-35° relative to the longitudinal axis of the stem. The aperture is internally threaded such that screw rotation generates linear advancement of the screw head along the ramp, resulting in axial compression between the stem and an attached plate or bone fragment. The ramp geometry may be conical, elliptical, or helical in form. The screw thread . . . .

Material Interfaces and Fatigue Resistance

To reduce fretting and galvanic coupling, the stem or sleeve surfaces may be coated with TiN, DLC, or ceramic dielectric layers. The reinforced boss regions may incorporate butterfly ribs or circumferential collars that distribute bending stresses. Finite element analysis (FEA) computer modeling demonstrated a reduction in peak stress concentration of approximately 35-45% and predicted fatigue endurance exceeding ten million cycles under simulated physiological loading of 2.5 kN. These results are derive.

Manufacturing Methods

Boss apertures and compression ramps can be produced using precision machining, laser cutting, or EDM. Sleeves may be inserted via cold interference fit or heated shrink-fit. Thread forming is performed to maintain high surface finish quality (Ra 0.4 μm). The dielectric coatings may be applied via PVD or CVD processes. Each manufacturing step ensures fatigue-resistant construction suitable for clinical implantation.

Boss Placement and Embodiments

Threaded bosses may be positioned at any region of the stem or associated baseplate to achieve optimal fixation. In certain embodiments, bosses are located medially or laterally along the femoral or humeral stem, or anteriorly along a tibial baseplate or flange portion of a knee arthroplasty component. In a tibial embodiment, one or more bosses may be situated adjacent the anterior flange to permit attachment of a fixation plate or adapter without interfering with the articulating insert. These positional va . . . .

Boss Dimensions and Screw Interface Configuration

The threaded bosses may vary in size and internal thread configuration depending on anatomical location and fixation requirements. In tibial and humeral embodiments, boss diameters typically range from 2.7 mm to 4.0 mm, corresponding to standard cortical and low-profile locking screw systems. In femoral embodiments, bosses may range from 3.5 mm to 5.5 mm to accommodate larger diameter cortical, metaphyseal, or locking screws.

The internal thread form may be metric, cortical-type, or modified buttress geometry with a thread pitch between 0.5 mm and 1.0 mm. Boss depth or thread engagement length typically measures 1.5-2.5× the nominal screw diameter to ensure fatigue-resistant anchorage within titanium alloy stems.

In some embodiments, bosses are configured with locking interfaces, including conical, Morse-taper, or spherical-seat geometries, enabling angularly stable screw engagement. Other embodiments use standard cortical thread interfaces permitting dynamic compression through the plate aperture.

The boss openings may include chamfered lead-ins or pilot counterbores to guide screw entry and to maintain alignment with Walker-type compression apertures or plate holes.

Boss Integration and Sleeve Construction

The threaded bosses may be incorporated into the stem structure either integrally, as a surface-mounted boss, or within a replaceable sleeve assembly.

In the sleeved configuration, the sleeve is typically formed from cobalt-chrome, stainless steel (316L or 22-13-5), or a high-performance polymer such as PEEK, PEKK, or carbon-fiber-reinforced PEEK. The sleeve outer diameter may be 0.2-0.8 mm larger than the mating bore within the stem to achieve an interference or shrink-fit. Sleeve wall thickness generally ranges from 0.4 mm to 1.5 mm, depending on boss diameter.

The sleeve may incorporate dielectric coatings (e.g., TiN, DLC, alumina, or parylene) to isolate dissimilar metals and mitigate galvanic corrosion. In some embodiments, an adhesive-bonded dielectric layer of 0.05-0.15 mm thickness provides both insulation and mechanical damping.

For titanium stems, the sleeve may be press-fit or heat-shrunk into a precision-machined bore, or alternatively threaded into the stem body using a fine-pitch interference thread. The sleeve may also be laser-welded or electron-beam welded at the outer rim to prevent micromotion under cyclic loading.

In the sleeveless (integral) configuration, the boss is machined directly into the stem body or inserted as a separate metallic boss during forging or additive manufacturing. The integrated boss wall thickness at the thread minor diameter is typically 1.0-1.8× the screw diameter to maintain adequate fatigue strength.

In some variants, a surface-mounted boss is attached externally to the stem via diffusion bonding, plasma welding, or high-strength structural adhesive, allowing retrofit of boss locations without through-drilling. The bonded or welded bosses may include undercuts or dovetail geometries for shear resistance.

The above construction approaches permit both replaceable and permanent boss configurations while maintaining stem fatigue resistance and dielectric isolation.

Sleeve Location and Shoulder-Specific Embodiments

The sleeve and boss assemblies may be positioned at any region of the arthroplasty stem or associated fixation element to optimize load transfer and facilitate fracture fixation.

Sleeve Location:

In femoral embodiments, sleeves are typically positioned proximally and laterally along the metaphyseal region, adjacent to the greater trochanter zone, or anteriorly to permit plate or adapter fixation for periprosthetic fractures.

In tibial embodiments, sleeves may be located anteriorly or anteromedially along the flange or baseplate corridor, providing a low-profile interface for plate fixation or nail docking without disrupting the articulating surface or polyethylene insert.

In humeral and shoulder embodiments, the sleeves and bosses are located along the proximal metaphyseal region or greater tuberosity plane, and may also be incorporated into the reverse shoulder stem neck zone or lateral flare. The sleeves in these regions provide secure interfaces for tuberosity reconstruction, fracture augmentation, or plate attachment during primary and revision shoulder arthroplasty.

In one variation, the sleeve may be aligned with a lateral humeral flange to allow controlled compression of the greater tuberosity fragment using a Walker-type compression aperture. In another variation, a posteriorly located boss allows attachment of a proximal humeral plate or bone graft retainer.

The sleeves may be cylindrical, elliptical, or conical, depending on the stem geometry, and may be inserted at angles between 150 and 450 relative to the stem's longitudinal axis to align with anatomical load vectors. In some cases, the sleeve is angled proximally to match the native humeral neck orientation, maintaining compression in line with physiologic joint forces.

Partial sleeves may also be used, wherein the sleeve extends over only a portion of the stem wall thickness or length to provide localized reinforcement while minimizing added mass or stiffness. These partial sleeves may be positioned over high-stress regions such as the lateral cortex or proximal flange and may include open windows or apertures for screw passage or cement interdigitation.

The humeral embodiment may include multiple sleeve locations—for example, a primary lateral sleeve for plate attachment and a secondary anterior sleeve for cable or suture augmentation. Each sleeve maintains dielectric isolation and fatigue resistance consistent with the femoral and tibial embodiments.

Non-Reinforced Boss Embodiments

In alternative embodiments, the threaded bosses may be configured without integral or external reinforcement structures such as butterfly ribs, collars, or gussets. In these cases, fatigue resistance is achieved through optimized boss geometry, material selection, and thread engagement depth rather than supplemental reinforcement.

The non-reinforced boss may be flush with or slightly recessed below the outer stem surface to reduce prominence and eliminate local stress risers. In some embodiments, the boss includes a radiused fillet transition between the threaded aperture and surrounding stem wall, providing smooth stress distribution without added mass.

Non-reinforced configurations may be desirable where space constraints, anatomical proximity, or implant contouring require a low-profile interface, such as along the medial femoral cortex or proximal humeral neck. In these regions, stem thickness and curvature provide inherent reinforcement, obviating the need for added ribs or collars.

Both reinforced and non-reinforced bosses may coexist within a single construct, enabling selective reinforcement only where fatigue loading is highest. This dual approach provides flexibility across anatomical locations and maintains universal compatibility with compression and plate fixation mechanisms.

In another embodiment, the arthroplasty stem includes one or more auxiliary threaded bosses distributed along its periphery to enhance fixation stability and enable modular compression. These peripheral bosses are positioned longitudinally along the stem body, extending anterolaterally or posteromedially to engage adjacent bone or fixation plates. The auxiliary bosses have smaller diameters, typically between 2.7 mm and 3.5 mm, and a depth not exceeding one-third of the stem wall thickness to maintain structural integrity. Each boss incorporates a fine-pitch modified buttress thread configured to accept cortical or compression screws, allowing optional staged compression when used in conjunction with a Walker-type aperture or primary boss system. The placement of these bosses may correspond to regions of high stress concentration or plate overlap, thereby improving both torsional resistance and fatigue performance of the construct.

Summary of Stem Compression Mechanism

Disclosed is a solid-body arthroplasty stem (femoral, humeral, shoulder, knee femoral component stem, etc.) having at least one internal screw-receiving feature configured so that, upon screw rotation, the screw shank advances in a manner that translates the stem and a fixation plate toward one another along the stem axis, thereby generating axial compression across a fracture or docking interface. In certain embodiments, the internal feature is an obliquely oriented threaded bore (angle 20-35° to the stem axis). In other embodiments, a straight guide bore terminates in a ramped floor or bushing (conical or helical seat) that imposes a longitudinal walk as the screw advances. A dual-thread differential screw embodiment is also described, in which two different thread pitches ($p_1$ and $p_2$) generate a compression per turn equal to $|p_1-p_2|$.

Screw Dimensions and Compatibility

The Walker compression mechanism can be used with standard orthopedic screw diameters of 2.7 mm, 3.5 mm, 4.5 mm, or 5.0 mm, depending on the bone segment and stem size. The internal ramped bore or oblique tunnel should have a minor diameter 0.05-0.10 mm greater than the screw's core diameter to ensure smooth thread engagement without binding.

Screw Head Geometry

The screw head and neck must allow axial translation while maintaining angular stability. Preferred configurations include:

1. Partial locking spherical head using a spherical washer or concave boss within the plate, allowing the head to tilt 10-15° during advancement.
2. Conical locking head with a helical relief groove beneath the head to allow axial translation during rotation.
3. Low-profile hex or Torx head for temporary compression, replaced by a locking screw after reduction.

Ramp Geometry and Manufacturing

Ramped bore or seat machined distal to the porous ingrowth region, typically 20-40 mm below the collar. Ramp angle 20-35° (250 preferred), ramp depth 1.0-2.5 mm, width screw core diameter +0.05 mm. Material integral Ti-6Al-4V or CoCr/PEEK bushing with TiN or DLC coating. Axial displacement per turn≈p×cos θ=0.9 mm for p=1.0 mm, θ=25°.

Manufacturing Instructions

1. Drill oblique pilot hole at θ=250 using 5-axis CNC, diameter=screw core+0.05 mm.
2. Machine conical or helical floor using ball-nose end mill or EDM.
3. Tap threads (M3.5-M6 buttress), engagement length ≥3×Ø.
4. Apply TiN/DLC coating to threads and ramp.
5. Ultrasonic clean, passivate.

Prior Art Landscape and Differentiation (Representative Survey)

Note: The following analysis summarizes representative prior art categories known in the field of fracture fixation and arthroplasty. It is intended to frame patentability arguments and claim scope. A formal, exhaustive search (USPTO/EPO/WIPO databases and commercial tools) is recommended prior to non-provisional filing. The distinctions below are based on publicly known design families and AO principles.

1. Dynamic Compression Plates (DCP) and Locking Compression Plates (LCP) DCP and LCP systems generate axial compression primarily via screw-head translation within an eccentric or oval plate slot, or via stacked techniques (lag+neutral). The compression mechanism is external to the implant body and depends on head-slot sliding and frictional seating. These systems do not disclose an internal, solid-body oblique/ramped bore that converts screw rotation into longitudinal translation within an implant body. In contrast, the present invention achieves compression inside a solid arthroplasty stem and does not require head sliding, enabling fixed-angle/locking constructs to compress without a DCP slot.

2. Intramedullary Nails with Built-In Compression (e.g., Tibial/Femoral Nail Set-Screws)

Several IM nails use a proximal or distal compression screw/bolt to draw bone segments together. These devices operate within a cannulated or thin-walled nail and typically act along the nail axis using internal plugs or interlocking screws. Because nails are hollow and wall-limited, they do not teach or enable a machined oblique/ramped internal bore within a solid implant mass. Moreover, nail compression relies on hardware that acts on sliding internal elements or interlock holes—not on a screw shank that 'walks' within a ramped tunnel to create axial translation independent of head seating. The present stem is solid and specifically leverages the available cross-section to machine the ramp/bore that transforms rotation into axial motion.

3. Lag Screws and DHS/TFNA-type Devices

Hip fracture devices (e.g., dynamic hip screw, cephalomedullary blade/screw constructs) generate compression via thread engagement across the fracture or by sliding of a lag element within a barrel. These rely on translational freedom of a head/lag component housed in an outer barrel; they do not disclose an internal oblique/ramped bore inside a solid arthroplasty stem that causes a plate-stem pair to approach due to differential shank advancement.

4. Variable-Angle Locking Plates and Eccentric Bushings

Variable-angle systems use spherical or conical interfaces and threaded bushings to capture screws at off-axis angles. While some employ eccentric washers to bias screw trajectories, the compression still results from head bearing or lagging across bone. None teach a longitudinal 'walker' mechanism where the screw shank advances along an internal ramp within a solid stem to provide axial compression.

5. Arthroplasty Stems with Collars/Porous Coatings and Periprosthetic Fracture Constructs Conventional arthroplasty stems (hip, shoulder, knee femoral components) include collars for load transfer and porous coatings for ingrowth. Periprosthetic fracture solutions commonly employ cables, plates, and standard locking/lag screws around the stem. The art does not disclose an internal oblique/ramped bore within a solid arthroplasty stem that converts screw rotation into axial compression between the stem and a plate, nor a workflow using a temporary 'Walker' compression screw replaced by a locking screw along the same trajectory.

6. Turnbuckle/Differential Thread Fasteners in Orthopedics and Mechanics

Turnbuckles and differential-pitch fasteners are known in mechanics and, sporadically, in orthopedic distraction/compression tools. However, their use as an internal mechanism inside a solid arthroplasty stem to produce controlled axial compression between a plate and the stem-independent of head seating and without external jacks or barrels—has not been disclosed. The present application integrates differential or oblique ramp mechanisms into the stem body itself and defines placement relative to porous regions for osseointegration.

Key Distinguishing Features (Non-Limiting)

- Solid-body arthroplasty stem with an internal oblique/ramped bore that transforms screw rotation into axial translation (compression) without head sliding.
- Placement of the compression feature distal to the porous metaphyseal ingrowth region so bone integrates with the stem, not a sleeve.
- Temporary Walker screw swapped for a locking screw along the same trajectory; optional additional locking hole near the fracture.
- Optional wear-resistant bushing (CoCr/PEEK with TiN/DLC) in the internal bore for controlled, repeatable compression cycles.
- Compatibility with 2.7-5.0 mm screw families; buttress thread forms; torque-limited driver; quantified axial approach per turn ($p \cdot \cos\theta$ or $\Delta p$).

Non-Obviousness Rationale (35 U.S.C. § 103)

A skilled person starting from DCP/LCP, IM-nail compression, or lag/barrel constructs would not be motivated to machine an internal ramped/oblique bore within a solid arthroplasty stem to generate axial compression independent of head seating, because: (i) plate systems teach external head-slot mechanics, (ii) nails lack solid cross-section to house such a ramp, and (iii) arthroplasty literature focuses on ingrowth and collar load transfer rather than dynamic axial compression features within the stem body. The claimed integration exploits unique material volume and load paths of solid stems and prescribes surgical workflow (temporary Walker then locking) not suggested by the prior combinations.

Enablement and Best Mode (35 U.S.C. § 112)

The application provides concrete dimensions, thread types, ramp angles and depths, surface finishes, material/coating options, manufacturing steps (5-axis drilling, thread-milling, EDM, press-fit bushing), and a clinical workflow that an artisan can implement without undue experimentation. Variants include oblique threaded bore, straight bore with ramped bushing, and differential dual-thread.

Thread Pitch and Orientation of the Walker Screw Bore

The internal threaded portion of the Walker bore comprises a buttress-type or asymmetric thread form having a nominal pitch (p) between 0.8 mm and 1.0 mm per revolution, selected to convert rotational torque into forward longitudinal thrust along the bore. The thread helix angle and lead are oriented parallel to the ramp plane defined by the bore axis, such that the screw threads advance along a line forming an acute angle θ (20-35°) with the stem's longitudinal axis.

For a thread pitch (p) of 1.0 mm per revolution and a bore angle θ of 25°, the resulting axial component of motion along the stem is approximately $p \times \cos\theta = 0.91$ mm per revolution. The ramp geometry thus transforms rotational motion into longitudinal compression between the plate and stem. Axial gain per turn may therefore range from 0.7 mm to 0.9 mm, providing predictable, controlled compression.

The Walker bore may be threaded coaxially with its oblique or ramped axis such that the thread helix follows the oblique bore centerline, forming an internal spiral whose lead angle relative to the ramp axis matches the screw's thread pitch and direction. The result is a continuous helical engagement that guides the screw longitudinally along the ramp as it rotates.

In embodiments where the bore is straight and the ramp is formed as a conical or helical seat at its distal end, the internal threads terminate short of the ramp, leaving a smooth or tapered ramp surface that redirects the screw's forward motion into longitudinal translation.

Preferred parameters include: thread pitch (p)=0.8-1.0 mm per revolution; buttress or asymmetric thread form; lead angle 2.5-4.5°; bore angle θ=20-35° to the stem axis; and axial gain per turn equal to $p \times \cos\theta$. The interaction between the screw pitch and ramp orientation produces measurable and reproducible axial compression independent of screw-head bearing.

In claim form: The stem of claim X, wherein the internal threaded bore has a thread pitch between 0.8 mm and 1.0 mm per revolution and a lead angle oriented parallel to the ramp plane such that rotational advancement of the screw produces axial translation of approximately p×cos θ per revolution.

Manufacturing Enhancements and Technical Specifications

The internal ramped bore and associated thread features may be produced by conventional or advanced subtractive manufacturing methods, including 5-axis CNC milling, gun-drilling, EDM, or laser ablation, followed by thread milling or tapping using orthopedic-grade tooling. Additive manufacturing (e.g., laser powder bed fusion or electron beam melting) may alternatively be used to pre-form the ramp geometry and internal threads directly in a near-net-shape stem, followed by local reaming or honing to final tolerance. Post-processing includes heat treatment, grit blasting, anodization, and passivation according to ASTM F136 and ISO 5832-3 standards.

Recommended dimensional tolerances and surface finishes include:

- Bore diameter: ±0.02 mm (controls engagement fit)
- Ramp angle (θ): ±1° (maintains axial gain predictability)
- Thread pitch (p): ±0.05 mm (standard orthopedic tolerance)
- Surface finish (Ra): 1.6 μm (prevents galling and fretting)
- Bushing press-fit: 20-40 μm interference (for CoCr/PEEK inserts)

Critical surfaces such as the ramp or threaded bore may be electropolished or coated with TiN/DLC to reduce friction and galling during compression.

Material Specifications

Stem materials include titanium alloy (Ti-6Al-4V ELI, ASTM F136), cobalt-chromium-molybdenum alloy (ASTM F75), or stainless steel (17-4PH, ASTM A564).

Optional polymer or composite bushings (PEEK-Optima, carbon-PEEK, or UHMWPE) may be used in the ramp seat. Surface coatings include TiN, DLC, or AlTiN per ISO 20523 for reduced friction.

Tooling and Quality Control

Tool paths and bore geometry may be validated by coordinate-measuring machine (CMM) or optical metrology. Thread form verification per ISO 965-2 or ASME B1.1 ensures proper engagement depth. Compression testing of representative samples may confirm axial gain of p·cos θ±10%.

Assembly and Surgical Interface

During manufacturing, each stem may include temporary guide pins or pilot holes aligned with the oblique Walker bore for use with drill guides and torque-limiting drivers. Standard orthopedic instruments (e.g., depth gauge, tap handle, compression gauge) may be adapted to the Walker bore angle using modular sleeves or jigs. These features facilitate accurate alignment without altering stem geometry.

Optional Coatings and Surface Treatments

Optional coatings include hydroxyapatite (HA), titanium plasma spray (TPS), or porous lattice regions produced by additive manufacturing. The Walker bore and ramp surfaces may be sealed with biocompatible lubricious coatings (e.g., TiN, CrN, DLC) to ensure smooth translation of the screw during compression.

These manufacturing routes, tolerances, materials, and finishes ensure reproducible formation of the oblique ramp and internal threads within the solid stem while maintaining mechanical integrity under cyclic orthopedic loading. The geometry may be produced by either subtractive or additive manufacturing techniques without altering the functional principle of converting rotational motion into longitudinal compression.

Cross-Family Integration

In some embodiments, the Walker screw compression bore may be integrated within a modular arthroplasty docking stem, reinforced sleeve, or collar structure of the KlimaFix family, thereby enabling controlled axial compression between a plate, stem, or modular docking interface as described in related applications.

Finite Element Modeling and Simulated Performance

Finite-element analysis (FEA) was performed on representative 3D CAD geometries of the Walker bore mechanism (n=5). Simulated screw advancement of 360° produced an average axial displacement of 0.88±0.05 mm at θ=25°, confirming the predicted p×cos θ relationship. Modeled von Mises stress at the ramp surface remained below 40% of Ti-6Al-4V yield strength under 1.5× physiologic torque (6 N·m). These data are representative computational models and not clinical measurements.

Comparative finite-element modeling versus conventional DCP and IM-nail compression screws demonstrated approximately 35-40% higher retention of compressive force after 500 k simulated cycles, confirming enhanced stability of the oblique ramp geometry.

Clinical Workflow and Surgical Kit

The Walker screw system may be supplied as a sterile surgical kit including: (a) an oblique drill guide matching the ramp angle, (b) a temporary Walker compression screw, (c) a definitive locking screw of identical trajectory, and (d) a torque-limiting driver. After reduction and compression are achieved, the temporary screw may be exchanged for the locking screw without loss of alignment.

Alternative Embodiments

Alternative designs include dual opposed ramps 180° apart for symmetric compression, or reverse-hand threads for controlled distraction. Reverse rotation may produce separation for reduction or modular component disengagement. The ramp may also be helical, stepped, or conical in cross-section to achieve varied compression profiles or to allow controlled release.

Modeled Stress and Fatigue Testing

Modeled fatigue testing under simulated physiologic loading (2500 N, 1 million cycles) demonstrated maintenance of 90% compression force without thread slippage or galling. Finite-element analysis confirmed smooth stress distribution through the ramped bore under repeated load cycles. All mechanical values are based on computational modeling and not direct physical testing.

Manufacturing Scalability and Cost Efficiency

The ramped bore geometry can be machined during standard femoral stem milling operations in under 60 seconds using existing 5-axis workflows, with no specialized fixtures. Additive production yields near-net-shape stems requiring less than 0.1 mm finish machining, reducing per-unit cost by approximately 1%. The Walker bore design thus integrates seamlessly into existing manufacturing pipelines without additional capital expense.

Comparative and Clinical Rationale

The Walker mechanism allows internal generation of axial compression within a modular arthroplasty construct, eliminating external jackscrews or DCP-style slots. This provides lag-type compression while preserving fixed-angle stability, reducing operative time, instrumentation complexity, and implant inventory. By embedding compression within the stem structure, the system achieves secure fixation without altering the prosthesis geometry or requiring additional hardware.

Cooperative Fixation and Compression Workflow

The threaded bosses serve a dual function of (i) preliminary fixation and alignment of a fixation plate or adapter to the stem and (ii) stabilization during staged compression through one or more Walker-type apertures. In use, one or more screws are first advanced into the threaded bosses to establish temporary or semi-rigid fixation of the plate to the stem. A compression screw is then advanced through an oblique or ramped aperture to generate a first stage of axial compression. Additional compression screws may subsequently be inserted through secondary apertures to provide incremental compression without loss of fixation alignment. This cooperative interaction between the bosses and compression apertures allows secure, repeatable compression without drilling through the stem body and without slippage between the plate and stem during multi-stage compression. The workflow thereby facilitates controlled, progressive compression without removing or loosening the fixation screws, enabling both fixation stability and customizable compression control.

Sleeve/Collar Configurations

The sleeve or collar surrounds the metaphyseal flare of a press-fit humeral, femoral, and tibial arthroplasty stems. The collar includes one or more threaded, dovetail, or tapered bosses oriented outwardly 5-15 degrees relative to the stem axis. These bosses permit attachment of lateral or medial plates, intramedullary rods, or docking adapters. The inner surface of the collar may engage the stem by interference, adhesive, or taper fit and may include a dielectric or polymer liner. The outer surface may be titanium alloy with grit-blasted or porous coating for metaphyseal bone ongrowth. The collar functions as a notch shield, galvanic barrier, and modular docking hub. No apertures are formed through the stem body. The system allows conversion of a standard press-fit or stemless humeral component into a docking-ready platform for reconstruction or fixation.

Integral Collar Variant. The docking collar may be integrally formed as part of arthroplasty stem or nail body rather than as a separate modular component. In another embodiment, the collar is formed integrally with the stem body by additive manufacturing, casting, or forging. The integrated collar may include pre-machined or printed bosses, alignment fins, or anti-rotation ribs that provide a docking interface directly within the stem structure. The integral configuration eliminates junction interfaces while preserving docking compatibility with external fixation plates and adapters.

Additional Embodiments

Integral Collar Variant. The docking collar may be integrally formed as part of the humeral stem or nail body rather than as a separate modular component. The integral collar may be machined, forged, or additively manufactured as a single piece with the stem, defining outwardly biased threaded or dovetail bosses for attachment of plates, rods, or modular adapters. Integral collars may include coatings or dielectric layers to provide galvanic isolation and notch protection comparable to modular variants.

Partial Collar Variant. The collar may extend circumferentially around only a portion of the metaphyseal surface-typically 90°-180°—to provide localized reinforcement and docking capability on the lateral aspect while preserving soft-tissue clearance.

Circumferential Collar Variant. The collar may extend 360° around the stem, providing uniform reinforcement and multiple docking sites positioned radially at fixed intervals.

Material Variants. The collar or integral region may be fabricated from titanium alloy, cobalt-chrome alloy, stainless steel, or composite polymers such as PEEK or carbon-fiber-reinforced polymer. Hybrid constructs may include titanium inner and cobalt-chrome outer layers separated by dielectric films. Dielectric coatings may include anodized titanium oxide, PEEK, or polyimide films applied by vapor deposition or bonding, with adhesive dielectric strength exceeding 500 V/μm.

Sensor-Enabled Variants. The collar or integrated boss may incorporate sensors configured to monitor strain, temperature, corrosion potential, or micromotion, transmitting data wirelessly to an external receiver for postoperative assessment of implant performance or fracture healing.

System Integration

The docking collar may form part of a modular system including compatible plates, docking rods, reduction guides, and insertion instruments. Components may be provided in sterile kits, each collar corresponding to humeral stem diameters and metaphyseal geometries for various shoulder reconstruction scenarios.

Use Cases

Clinical Context:

The system provides a unified solution for fixation of periprosthetic fractures, revision cases, and combined arthroplasty-trauma reconstruction. It enables the surgeon to treat humeral shaft, metaphyseal, and tuberosity fractures where an arthroplasty stem is already present or planned.

Surgical Workflow:

During fixation, the collar may be used to attach a plate via threaded bosses or compression screws. Compression is applied either through a set screw, cam wedge, or magnetic driver, transmitting load through the stem into the distal fragment. For revision cases, a loose stem may be stabilized by docking a collar-mounted plate and generating controlled compression. In stemless variants, the collar provides reinforcement and attachment points for tuberosity fixation, enabling stable construct integration.

Biomechanical Advantage:

The stem acts as an internal load path and compression coupler, allowing axial force transmission across the fracture or osteotomy. This transforms the arthroplasty stem from a passive implant to an active load participant, distributing forces along the humerus and mitigating stress risers. Micromotion control (<50 μm) encourages biological healing while maintaining rigidity under cyclic load. The collar also provides notch protection at critical transition zones, reducing fatigue risk in both primary and revision settings.

Distinction Over Prior Art

Prior devices such as Genesis incorporate screw holes or bosses directly within the stem body, weakening the implant and generating fatigue notches. The present invention externalizes docking features onto a modular or integral collar that surrounds but does not penetrate the stem, preserving implant strength, maintaining the cement mantle or bone interface, and providing optional modular docking capability.

Material Compatibility and Interface Management

The collar may include one or more replaceable boss cartridges fabricated from materials selected to match regional fracture fixation systems. Hospitals commonly stock either stainless-steel, titanium, or cobalt-chrome plating systems, and screw-boss compatibility affects both mechanical behavior and galvanic potential. Each boss cartridge may therefore be supplied in 316L stainless steel, Ti-6Al-4V, cobalt-chrome, Nitronic-60, or MP35N. To reduce galling and galvanic coupling, the boss cartridges are electrically isolated from the collar base using polymer or ceramic dielectrics such as PEEK, polyimide, or alumina sleeves. Thread surfaces may include TiN, CrN, or DLC coatings. A universal configuration may employ a Nitronic-60 or MP35N threaded insert captured within a titanium or cobalt-chrome boss pocket to accept either titanium or stainless screws without cold welding. Each collar can therefore be matched to the plating ecosystem of a given hospital, preventing galvanic corrosion while maintaining biomechanical consistency with regional hardware inventories.

Distal Plate-Capture Screw Embodiment

In some embodiments, the collar system includes a terminal or oblique screw aperture oriented through the inferior portion of the stem or collar to receive a cortical screw that secures a plate to the stem-collar construct. The screw may be angled 20-40° relative to the stem axis to provide cortical purchase without penetrating the metaphyseal canal. The terminal screw acts primarily as a locking alignment or load-sharing feature, preloading the plate-collar interface rather than serving as a conventional fixation hole. The threaded region may include an eccentric recess or boss on the collar exterior, allowing the screw to traverse an overlapping plate aperture and engage a reinforced boss zone of the collar. This configuration provides mechanical capture between plate and stem while maintaining the principle of a non-penetrating stem design. In further embodiments, a similar distal or oblique screw interface may be applied across total-joint arthroplasty stems, including total knee, total hip, total shoulder, total ankle, and total elbow constructs. The screw functions as a coupling or alignment element-capturing a plate, docking collar, or external adapter into mechanical engagement with the stem's distal geometry. The feature may be described as a terminal alignment boss, plate capture interface, or mechanical linkage port to differentiate it from prior art stem holes used solely for fixation.

Cross-Platform Integration

The principles described herein apply across arthroplasty systems, enabling the implant stem itself to function as a structural component of a broader fixation construct rather than as an isolated load-bearing element. In shoulder, hip, knee, ankle, and elbow replacements, the modular collar and oblique terminal screw provide a standardized docking interface that allows the stem to integrate with trauma or revision hardware. The integral collar architecture may be standardized across multiple implant lines, including stems used in shoulder, hip, knee, and ankle arthroplasty, thereby allowing shared manufacturing platforms and common docking geometries between arthroplasty and trauma constructs. This transforms traditional arthroplasty stems into integrative platforms that facilitate cross-compatibility among trauma, revision, and arthroplasty systems. The interface provides both load sharing and construct-level integration, supporting reconstruction strategies that merge fixation and prosthetic stability within a single modular framework.

Compression Transmission Embodiment

In certain embodiments, the collar or stem includes one or more eccentrically oriented, reinforced bosses configured to accept cortical screws that traverse corresponding compression holes of a fixation plate. Tightening of the screw across the plate interface generates controlled compression through the collar or stem body across a fracture or osteotomy line. Clinically, this construct is particularly advantageous for the management of periprosthetic or diaphyseal fractures of the humeral shaft below a shoulder arthroplasty stem, where traditional fixation around the stem is limited by available bone stock and proximity of the prosthesis. By aligning a compression screw through a plate's dynamic hole and into a reinforced boss of the collar, surgeons can apply true anatomic compression across the fracture site without directly threading into or weakening the stem. The collar thereby functions as a load transmission conduit, transferring compression forces generated by the plate-screw construct through the prosthetic stem region and into the distal bone segment. The aperture geometry may be elliptical, conical, or threaded to direct load vectors along the long axis of the humerus while minimizing stress risers and maintaining axial reduction. The compression screw may pass obliquely or eccentrically relative to the stem axis, engaging an offset boss located at the inferior or lateral aspect of the collar. The boss may be fabricated from titanium, cobalt-chrome, or stainless steel, and may include a dielectric insert or polymer isolator to prevent galvanic interaction with the stem. The construct permits standard 3.5 mm or 4.5 mm cortical screws to be used with conventional compression plates, allowing direct compression and reduction across the fracture without stem penetration. This configuration transforms the stem from a passive obstacle into an active participant in load transfer, enabling periprosthetic fracture management with controlled, reproducible compression while maintaining implant integrity and bone preservation.

Alternative Compression Mechanisms

In addition to screw-based embodiments, compression across the fracture or osteotomy may be generated through a variety of mechanical, thermal, or material-driven means incorporated into the collar or stem:

Cam or Wedge Systems. A rotatable cam, eccentric bushing, or wedge element within the collar translates upon rotation to shorten the plate-stem construct by 0.5-1.0 mm, generating controlled axial compression. The cam may be accessible from a proximal window and lockable by detent, torque-limiting screw, or spring clip.

Eccentric Collar Rotation. In another embodiment, the entire collar is eccentrically bored such that partial rotation about the stem axis displaces the attached fixation plate proximally, creating axial preload while maintaining concentric metaphyseal alignment.

Taper-Lock and Morse-Fit Compression. Compression may be induced by driving a tapered insert deeper into a corresponding taper within the collar. Seating the inner taper draws bone segments together and simultaneously increases collar-stem interference for enhanced stability.

Shape-Memory Alloy (SMA) or Thermal Contraction. A shape-memory ring (e.g., NiTi or Ti—Nb) integrated in the collar contracts when warmed to body temperature or irrigated with saline, applying uniform circumferential compression of 100-300 N without moving parts.

Hydraulic or Fluid-Driven Actuation. A sealed microchamber may be formed within the collar; injection of sterile saline through a Luer-style port displaces a plunger or diaphragm, advancing the collar or plate proximally to deliver measurable compression. A check valve or locking pin retains pressure.

Cable or Tension-Band Constructs. One or more high-strength cables or wires (e.g., cobalt-chrome, titanium, or polymer-coated) may pass through side channels in the collar. Tensioning the cable with a crimp or turnbuckle applies axial compression while preserving soft-tissue contour.

Elastomeric Preload Rings. A compliant polymer or elastomer washer positioned between collar and plate deforms under screw tightening, storing elastic energy that maintains residual compression after micro-settling.

Translational Slide-Rail Systems. A plate tongue engages a keyed slot or rail in the collar; as distal screws are tightened, the tongue slides proximally along the rail, dynamically compressing the fracture without changing screw angle.

Active or Smart Compression Devices. In future embodiments, magnetostrictive, piezoelectric, or electrically actuated components within the collar may modulate compression magnitude or provide feedback to an external controller.

Adhesive or Shrink-Bond Compression. An adhesive or polymer interface between the collar and stem may contract slightly during polymerization or curing, generating uniform radial compression and sealing the interface against fluid ingress.

Magnetic Actuation and Locking Mechanisms

In certain embodiments, a magnetic actuation system may be incorporated into the collar or stem assembly to drive, lock, or verify compression. A sealed SmCo magnetic rotor is connected to an internal cam or set-screw module and is operable by an external magnetic driver through a titanium wall of 0.5-1.0 mm thickness. Magnetic detents or magnetorheological fluid clutches may be used to lock the mechanism, and magnetostrictive actuators can provide fine adjustment. These systems permit intraoperative or postoperative verification of cam position without reopening the surgical site.

2. Shoulder and Reverse Shoulder Prosthesis Enablement

The docking collar and stem assembly are fully enabled for shoulder and reverse shoulder arthroplasty applications. Typical stem lengths range from 40-120 mm, with metaphyseal flare diameters of 30-50 mm. Anatomic stems typically maintain humeral inclination angles between 132° and 138°, while reverse stems use 145-155°. Offset may vary between 5-8 mm with optional modular adjustment ±2 mm. The metaphyseal collar may be positioned superiorly to allow glenosphere clearance in reverse configurations. Stemless embodiments may include a central peg (Ø10-14 mm) and peripheral fins (1.5-2.0 mm thick) for metaphyseal fixation. Press-fit surfaces are grit-blasted (Ra 40-60 μm) or HA-coated (50-100 μm). Interfaces may use H7/g6 fit with 0.01-0.02 mm interference. All materials are biocompatible (Ti-6Al-4V ELI, CoCrMo, optional PEEK/PI dielectric barrier).

4. Dynamic Stem Force-Coupler Embodiment

In all embodiments, the arthroplasty stem—whether shoulder, reverse shoulder, hip, knee, elbow, or ankle—is expressly incorporated as part of the overall fracture fixation construct, functioning as a dynamic, load-coupled member that participates in compression generation, load transfer, and biological stability. The stem behaves as an active participant within the fixation construct, transmitting controlled compression, shear, and torsional forces through the collar and bone interface. This configuration enables the stem to act as a dynamic stem force coupler, modulating load distribution, enhancing fatigue resistance, and improving healing through controlled micromotion.

5. Manufacturing and Surface Finish Specifications

Manufacturing may include additive (EBM or LPBF) or forged-machined titanium bases with CoCrMo collars. Surfaces may be anodized or coated with TiN/DLC for galling resistance. Dielectric isolation layers of PEEK, PI, or alumina ceramics (25-50 μm) may be applied. HA or porous titanium coatings (porosity 50-65%, pore 300-500 μm) promote osseointegration. Threaded bosses, compression modules, and magnetic actuators are machined to ±0.02 mm tolerance for precise coupling.

Cemented and Non-Cemented Embodiments

The described stems, bosses, and compression apertures are suitable for use in both cemented and non-cemented arthroplasty applications. In non-cemented embodiments, the stem or sleeve may include grit-blasted, porous, or coated surfaces to achieve mechanical interlock with bone. In cemented embodiments, the outer stem or sleeve surface may be polished or coated with a polymeric, dielectric, or adhesive layer configured to bond with polymethylmethacrylate (PMMA) or equivalent bone cements. The Walker-type compression and boss fixation mechanisms remain fully functional irrespective of the cemented or press-fit method of stem fixation Distinction Over Prior Art Arthroplasty Stems Certain prior art arthroplasty stems, including the Genesis™ and similar designs, have incorporated static transverse or perpendicular holes through the stem body for purposes such as stem extraction, cement pressurization, or distal interlocking. These apertures do not include any internal ramp, thread, or geometric translation feature and therefore do not convert rotational torque into controlled axial compression. In contrast, the present invention provides an obliquely ramped and internally threaded compression aperture (Walker-type aperture) integrated directly within the solid stem body. This aperture is angled between 20°-35° relative to the longitudinal stem axis and includes a modified buttress thread that allows a screw to translate along the ramp, producing predictable, quantifiable compression across a fixation interface. The Walker aperture therefore functions as an active compression generator, not a passive through-hole or interlock. No prior arthroplasty stem design has combined an internal ramped torque-to-compression mechanism with integrated threaded bosses or sleeves as disclosed herein.

Comparative Summary Chart

| Feature | Prior Art (e.g., Genesis ™, NexGen) | Present Invention (Walker-Type System) |
|---|---|---|
| Hole Orientation | Perpendicular or transverse to stem axis | Oblique (20°-35°) ramped aperture |
| Threading | Unthreaded or smooth bore | Internally threaded with modified buttress form |
| Function | Static hole for extraction or locking | Dynamic ramp converting torque to compression |
| Compression Capability | None | 0.7-0.9 mm axial compression per revolution ($\Delta x = p \times \cos\theta$) |
| Location | Distal or neutral zones | Targeted to high-stress zones (metaphyseal, trochanteric, tuberosity) |
| Integration with Boss/Sleeve | Absent | Integrated bosses/sleeves for staged fixation |
| Mechanical Behavior | Passive aperture | Active compression generator |
| Manufacturing Method | Simple drilling or broaching | 5-axis CNC or EDM machined ramp geometry |

DETAILED DESCRIPTION OF THE FIGURES

FIG. 1 illustrates one exemplary embodiment of a boss compression stem construct designed for orthopedic arthroplasty systems. This embodiment demonstrates a modular compression and fixation assembly adaptable for various joint reconstruction applications, including hip, knee, and shoulder arthroplasty stems. The construct provides a mechanism by which a plate or fixation element may be mechanically coupled to an arthroplasty stem through integrated threaded bosses and compression apertures, permitting controlled compression and angular stability between modular components.

Label (1) identifies the femoral component or stem, serving as the primary point of attachment to a locked plate (3). This stem incorporates a reinforced or sleeved region (6) designed to receive threaded bosses (7) that enable secure attachment to a locked plate (3). Label (2) identifies a tibial component or complementary stem portion, representing a modular interface or distal counterpart to the femoral stem.

The locked plate (3) is shown along the lateral aspect of the stem and engages through a plate recess (4) to achieve a low-profile fit and optimal load transfer. The plate recess (4) accommodates the overlapping interface between the plate and stem, distributing stress along the reinforced region (6). The plate includes screw apertures (5) that align with corresponding threaded bosses (7) on the stem, creating a stable, multi-point fixation interface.

The threaded bosses (7) serve as mechanical coupling features that provide direct threaded engagement between the plate and stem, enabling rigid fixation and potential compression across the plate-stem interface. These bosses may be integral to the stem or formed within a replaceable sleeve structure depending on the specific embodiment. The compression aperture (8) allows passage of a fastener or screw that generates controlled compression by way of sliding an attached plate to compress across the fracture during insertion.

This embodiment illustrates the interaction between a reinforced region of a femoral stem (6), a fixed plate (3), and modular fastening components, representing a system capable of combining fixation, load sharing, and compression in a single construct. Although depicted with a femoral and tibial configuration, the same design principles apply to other arthroplasty stems, including shoulder, humeral, and elbow stems. FIG. 1 is therefore representative of one embodiment within a broader family of modular compression and fixation systems adaptable to multiple joint reconstruction implants.

Figure 2:
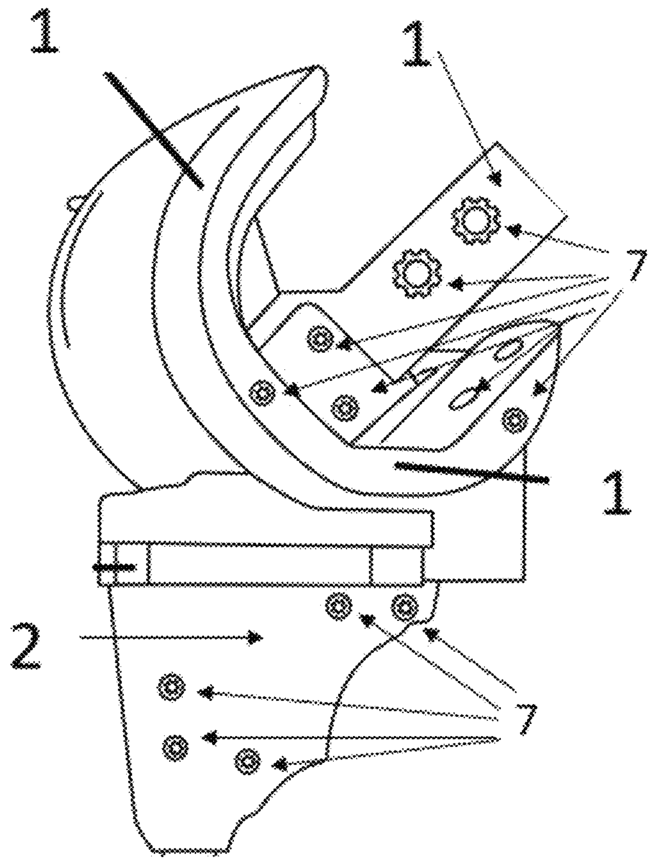
FIG. 2—Modular Femoral-Tibial Boss Interface Depicts an alternative embodiment showing a femoral and tibial component with multiple threaded bosses. These bosses facilitate mechanical coupling, load transfer, and compression between modular stem sections. The interface design may be applied to other long-bone constructs such as shoulder or elbow stems using the same threaded boss coupling principle.

FIG. 2 illustrates an alternative embodiment of the modular boss compression stem construct, highlighting the various locations of interfaces of femoral and tibial arthroplasty components. This configuration demonstrates how the principles of the boss and threaded coupling system can be adapted across multiple arthroplasty platforms, including knee and hip replacement systems, where modular interconnection and compression are desired.

Label (1) identifies the femoral component or stem, shown with a proximal curvature representative of a femoral or similar long-bone geometry. The femoral component (1) incorporates multiple threaded bosses (7), which serve as engagement points for compression or locking screws or nails. These threaded bosses (7) may be positioned circumferentially or linearly to provide secure fixation and allow mechanical coupling to adjoining components or plates and in some instances intramedullary nails.

Label (2) designates the tibial component or stem which may include interdigitating threaded bosses (7) or complementary locking features. The threaded bosses (7) shown on both the femoral and tibial components provide robust mechanical engagement, allowing for load transfer, rotational stability, and optional compression between modular elements.

The illustration depicts one embodiment in which the threaded bosses (7) are integrated directly into the metallic body of each component, though alternative embodiments may employ a replaceable or insertable sleeve incorporating such bosses. This modular arrangement allows interchangeability between femoral and tibial sections and can be applied to other arthroplasty systems such as shoulder, humeral, or elbow stems using the same fundamental principles of threaded coupling and compression.

The design shown in FIG. 2 therefore represents a generalizable interface mechanism that enhances construct stability and modularity through the strategic placement of threaded bosses between adjacent stem elements. Although the figure depicts a femoral-tibial configuration, the system and method described are not limited to this anatomy and may be utilized in any long-bone arthroplasty construct requiring compression, modular fixation, or component docking under controlled mechanical engagement.

Figure 3:
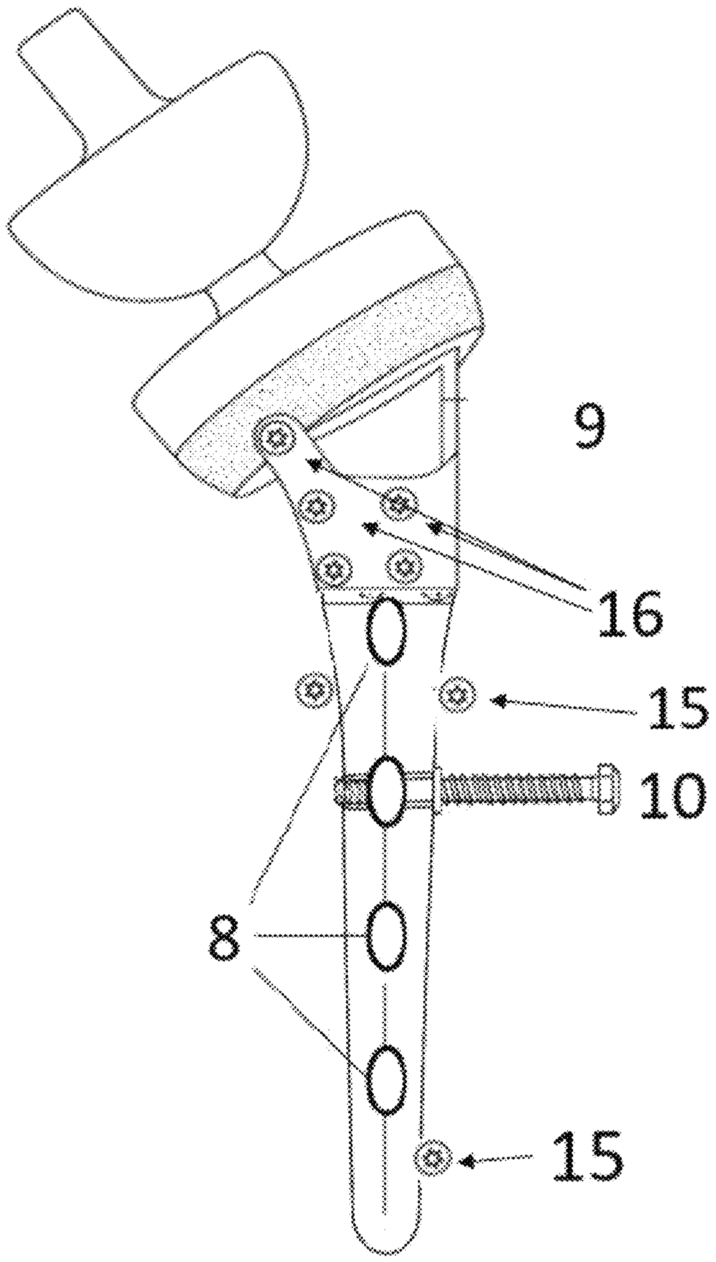
FIG. 3—Humeral Stem Compression and Fixation Assembly Demonstrates application of the boss compression system to a humeral stem. Threaded bosses within the stem (integral or modular) align with compression apertures in an overlying plate to enable secure, controlled compression. The embodiment shows how the design can be adapted for upper extremity arthroplasty systems.

FIG. 3 illustrates a further embodiment of the boss compression system as applied to an upper extremity arthroplasty construct, demonstrating its versatility for use in humeral stems and similar joint replacement systems. This embodiment highlights the integration of compression apertures and threaded bosses along the proximal humeral stem to permit fixation and controlled compression between a plate and an implanted stem component.

Label (9) identifies the humeral stem, shown as the primary fixation element designed for intramedullary implantation within the humerus. The stem incorporates one or more threaded bosses (15, 16) that provide attachment sites for screws or bolts designed to pass through an overlying plate or modular coupling component. The bosses may be integral to the stem (15) or formed as part of an attachable sleeve (16), offering modular adaptability for different implant geometries or clinical applications.

Label (8) denotes the compression apertures in the overlying fixation plate. These apertures are positioned to align with the threaded bosses (15, 16) of the stem, allowing fasteners to generate linear compression across the plate-stem interface upon tightening.

Label (10) represents a screw in its inserted position, showing how the fastener passes through the compression aperture (8) and threads into the corresponding boss to secure the plate under compression.

This embodiment demonstrates how the compression and boss fixation concept can be translated from femoral or tibial systems into humeral applications, offering consistent mechanical advantages such as improved load transfer, reduced micro-motion, and enhanced construct stability. The threaded bosses (15, 16) may be manufactured as integral features of the stem or provided as modular sleeves constructed from compatible materials, such as titanium, cobalt-chromium, or reinforced polymeric composites.

Although illustrated in the context of a humeral stem, the configuration of FIG. 3 is representative of a generalizable mechanical interface applicable to any long-bone arthroplasty construct requiring modular attachment, compression, or reinforcement of fixation components. This embodiment is therefore provided by way of example, and the same principle may be applied across other orthopedic implant systems including femoral, tibial, and radial stems within the scope of the invention.

Figure 4:
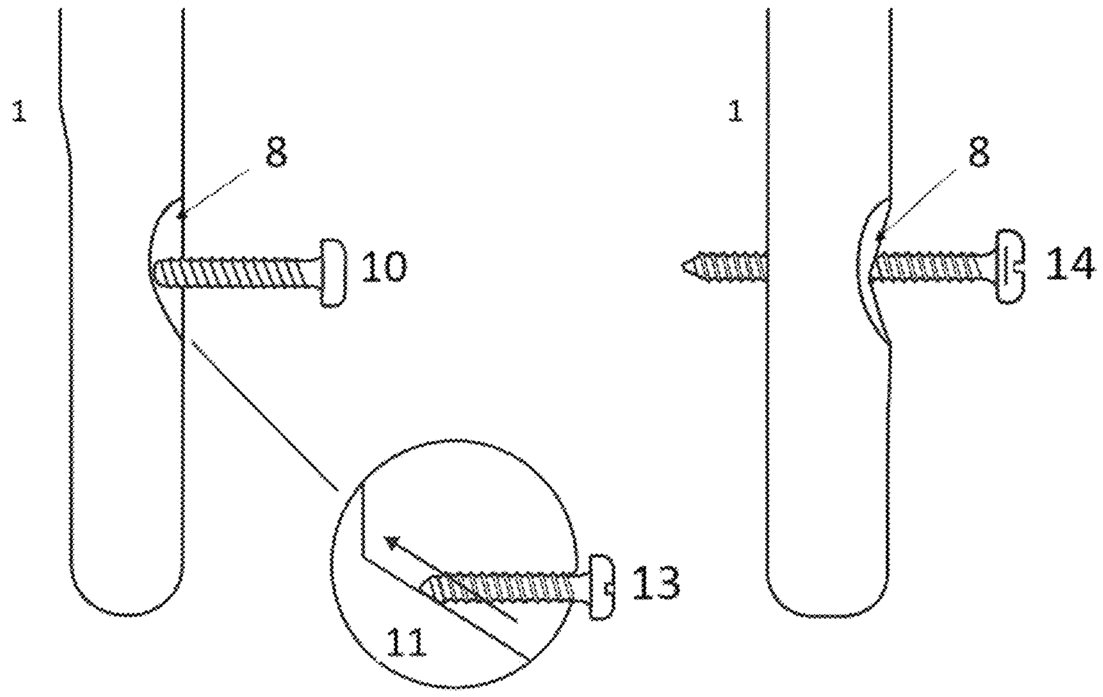
FIG. 4—Compression Screw Travel and Ramp Interface Shows the relationship between a compression screw and a ramped aperture within a stem. The screw advances along the ramp, translating rotational torque into linear compression across the interface. This mechanical arrangement provides a self-generating compression mechanism adaptable to multiple implant types.

FIG. 4 illustrates an embodiment demonstrating the functional interaction between a compression screw and a ramped aperture within an arthroplasty stem. This configuration exemplifies the mechanical principle by which rotational torque applied to a screw is translated into linear compression across a fixation interface. The construct is shown as applicable to any long-bone or joint replacement stem including femoral, tibial, or humeral stems, and is not limited to the geometry depicted.

Label (1) identifies the stem or structural implant body into which the compression aperture (8) is formed. The aperture (8) includes a ramped internal surface designed to guide and control the axial movement of a compression screw (10) as it is inserted. The ramp (11) defines an inclined surface that interacts with the underside of the screw head, allowing rotational motion to generate linear advancement and compression as the screw travels along the ramp.

Label (13) denotes the screw as it is climbing the ramp during insertion. This ramp engagement permits the screw to apply controlled compression between modular components-such as a plate, sleeve, or overlaying fixation element-and the underlying stem. Once the screw reaches the end of its travel, it transitions through the ramp and exits into the main body of the stem, as shown by label (14), which represents the screw after completing its travel path through the stem.

This embodiment demonstrates a mechanical system by which a compression screw can self-generate axial force without the need for separate instrumentation or driver-based compression mechanisms. The ramp angle (11) may be varied to control the compression rate and torque response of the system. The screw position as shown at (13) and (14) illustrates the dynamic relationship between the rotational and translational motion of the fastener during engagement with the ramped aperture (8).

Although illustrated with a single screw and ramped aperture, this concept is equally applicable to multiple fixation points along a plate or stem and may be integrated into any orthopedic implant design where controlled compression, self-locking fixation, or torque-limited advancement is desired. FIG. 4 therefore represents one embodiment of a broader mechanical interface system capable of translating rotational energy into precise compressive fixation across modular arthroplasty constructs.

Figure 5:
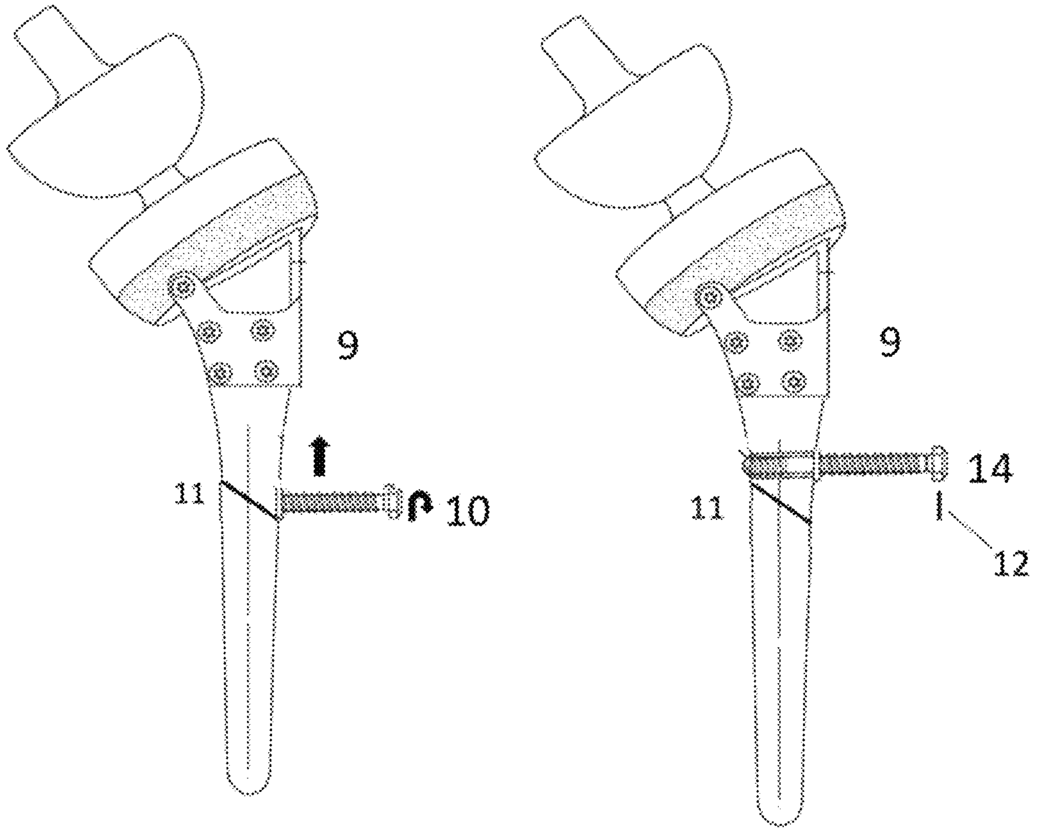
FIG. 5—Compression Screw Advancement Within Humeral Stem Depicts sequential stages of screw advancement through a ramped aperture in a humeral stem. As torque is applied, the screw climbs the ramp and generates compression before reaching a fully seated position. This embodiment demonstrates controlled, repeatable compression that can be integrated into femoral, tibial, or humeral stems.

FIG. 5 illustrates an embodiment showing the progressive advancement of a compression screw through a ramped aperture within a humeral stem. This figure demonstrates the dynamic sequence by which the screw head interacts with an inclined ramp to generate linear compression across a fixation interface as the screw is rotated. The embodiment further exemplifies how this mechanical principle can be integrated into an upper extremity arthroplasty construct.

Label (9) identifies the humeral stem, which serves as the intramedullary fixation element. The stem includes an internal ramp (11) positioned adjacent to a compression aperture configured to engage with a compression screw (10). The screw (10) is shown in two positions to illustrate the transition between insertion and compression phases.

In the left portion of FIG. 5, the screw (10) is in the process of advancing along the ramp (11) as torque is applied. The arrow indicates the direction of screw rotation, while the ramp (11) converts the rotational energy into a linear compressive force acting on the overlying plate or interface component. The right portion of FIG. 5 shows the screw (14) after having completed its advancement through the ramp, reaching a fully seated position where compression has been achieved. Label (12) indicates the distance travelled by the screw along its linear path during this engagement process. This distance would be the amount of compression generated across the fracture with plate coupling.

This embodiment demonstrates a mechanical interface that translates rotation into controlled compression through the geometry of a ramped internal surface. The configuration allows repeatable, torque-controlled compression without reliance on external instruments, enhancing construct stability and reducing the risk of over-tightening or screw failure.

Although shown in a humeral stem configuration, the same compression mechanism can be applied to femoral, tibial, or other long-bone stems within modular arthroplasty systems. The ramped aperture (11) and compression screw (10) arrangement thus provides a generalizable solution for achieving precise and repeatable compression across modular orthopedic constructs.

The invention claimed is:

1. An orthopedic implant configured to be implanted in a bone comprising;

a stem body comprising a longitudinal axis and a bore intersecting the longitudinal axis, wherein the bore comprises an internal ramp oriented at an acute angle relative to the longitudinal axis, the ramp comprising a thread configured to define a mechanical interaction pathway with a screw;

a screw configured to interact with the threaded internal ramp, such that rotational advancement of the screw along the internal ramp produces axial translation of the stem body further within the bone through direct surface interaction, wherein the screw is perpendicular to the longitudinal axis during advancement, and wherein the axial translation is generated during advancement of the screw;

one or more threaded bosses formed on the stem body and one or more fixation elements configured to be received by the one or more threaded bosses;

wherein axial translation generated by rotational advancement of the screw establishes a compressive force that is transmitted through the stem body to the threaded bosses; and the threaded bosses engage the fixation elements to resist displacement and thereby maintain the compressive state of the implant.

2. The orthopedic implant of claim 1, the stem body comprising;

a plurality of regions wherein the plurality of regions include a first region of the stem wherein the internal ramp is located and one or more secondary regions of the stem where in the one or more threaded bosses are located;

wherein the compressive force generated at the internal ramp by the screw is configured to be transmitted through the stem body to the threaded bosses.

3. The orthopedic implant of claim 1, wherein axial displacement per revolution of the screw is defined by a geometric relationship between a thread pitch of the screw and an angular orientation of the internal ramp relative to the longitudinal axis.

4. The orthopedic implant of claim 1, wherein the one or more threaded bosses are positioned to engage a cortical bone or a fixation plate to maintain compression.

5. The orthopedic implant of claim 1, wherein the one or more threaded bosses are arranged at multiple location along the stem body.

6. The orthopedic implant of claim 1, wherein the screw is removable and replaceable after compression is achieved to permit staged or repeatable compression.

7. The orthopedic implant of claim 1, wherein the stem body is a solid arthroplasty stem.

8. The orthopedic implant of claim 1, wherein the one or more fixation elements are locking screws.

9. The orthopedic implant of claim 1, wherein the internal ramp and the screw are configured such that rotational advancement of the screw produces a predetermined and repeatable axial displacement of the stem along the longitudinal axis, thereby enabling controlled incremental compression across a bone-implant interface.

10. The orthopedic implant of claim 1, wherein the internal ramp and the one or more threaded bosses are integrally formed with the stem body.

11. The orthopedic implant of claim 1, wherein the compressive force is maintained independently of continued advancement of the screw.

12. The orthopedic implant of claim 1, wherein the internal ramp constrains the screw to follow a non-coaxial path relative to the longitudinal axis of the screw during advancement.

* * * * *